US00PP23159P2

(12) United States Plant Patent
Kordes

(10) Patent No.: US PP23,159 P2
(45) Date of Patent: Nov. 6, 2012

(54) FLORIBUNDA ROSE PLANT NAMED 'KORMARKRON'

(50) Latin Name: *Rosa hybrida*
Varietal Denomination: KORmarkron

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,082

(22) Filed: Jul. 22, 2011

(51) Int. Cl.
*A01H 5/00* (2006.01)

(52) U.S. Cl. ..... Plt./150

(58) Field of Classification Search ..... Plt./150
See application file for complete search history.

*Primary Examiner* — Annette Para

(57) ABSTRACT

A new and distinct variety of rose with long lasting, novel medium red flowers, and attractive foliage with excellent disease resistance. It exhibits moderate growth and an upright to bushy bushy habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORmarkron'.

The new variety of rose plant of the present invention originated from a controlled crossing in a breeding program of two distinct parents during the summer of 2002. The crossing was between an 'un-named seedling' and 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORmarkron'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The flower color of 'KORmarkron' is medium red while the flower color of the seed parent it dark red.
2. The petal count of 'KORmarkron' is very double while the petal count of the seed parent is semi-double.

The new rose plant may be distinguished from its pollen parent, an 'un-named seedling' by the following combination of characteristics:

1. The foliage of 'KORmarkron' is semi-glossy while the foliage of the pollen parent is very glossy.
2. The disease resistance of 'KORmarkron' is excellent while the disease resistance of the pollen parent is average.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORmarkron' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORmarkron' was selected in May, 2003 from the seedling beds to be asexually propagated for further evaluation. The first asexual propagation of 'KORmarkron' was done by budding to seedling understocks in July, 2003 at the inventor's nursery in Offenseth-Sparrieshoop, Germany.

This initial and other subsequent propagations conducted in controlled environments demonstrate that 'KORmarkron' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORmarkron'.

DETAILED BOTANICAL DESCRIPTION

The following is a description of 'KORmarkron', as observed growing in July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORcasima', a rose variety from the same inventor described and illustrated in U.S. Plant Pat. No. 20,732 and issued on Feb. 9, 2010 are compared to 'KORmarkron' in Chart 1.

CHART 1

| Characteristic | 'KORmarkron' | 'KORcasima' |
|---|---|---|
| Average sepal size: | 25 mm (l) × 8 mm (w). | 18 mm (l) × 7 mm (w). |
| Average pistil count: | Approximately 15 present. | Approximately 35-40 present. |
| Average leaf size: | 160 mm (l) × 130 mm (w). | 125 mm (l) × 75 mm (w). |

Parents:

*Seed parent*.—An 'un-named seedling'.

*Pollen parent*.—An 'un-named seedling'.

Classification:

*Botanical classification*.—*Rosa hybrida* 'KORmarkron'.

*Commercial classification*.—Floribunda rose.

FLOWER AND FLOWER BUD

*Blooming habit*.—Continuous.

*Flower bud*.—Size: Upon opening, 20 mm in length from base of receptacle to end of bud and 18 mm diameter at its widest point. Bud form: Short. Globular. Bud color: As sepals first unfold, bud color is Red Group 46A. When ¼ open, the upper surface of petals is Red Group 46C, and the lower surface is Red Group 46B. Sepals: Color: Upper surface Yellow-Green Group 146D. Lower surface between Yellow-Green Group 146B and 146C and with intonations of Greyed-Purple Group 187C. Intonations on the lower surface more intense. Size: Average 25 mm (l)×8 mm (w). Shape: Triangular. Sepals generally subulate. Sepal apex is generally cirrose. Weak foliaceous appendages on two of the five sepals. Apex: Apiculate. Base: Flat at union with receptacle. Surface texture: Upper side: Strongly pubescent. Lower surface: Light pubescence. Margins: Pubescent, with limited numbers of stipitate glands.

*Receptacle*.—Surface: Smooth. Color: Yellow-Green Group 146C. Shape: Urn-shaped. Size: 10 mm (h)×9 mm (w).

*Peduncle*.—Surface: With stipitate glands. Length: 40 to 60 mm average length. Diameter: 1 to 2 mm average diameter. Color: Yellow-Green Group 146C. Strength: Moderately strong. Borne: Multiple flower buds per stem, generally 3 to 8.

Flower bloom:

*Fragrance*.—Light.

*Duration*.—On the plant 4 to 7 days. As a cut flower, 3 to 5 days. Senesced petals drop away cleanly.

*Size*.—Medium size for a floribunda rose. When open, the average flower diameter is 80 mm and the average flower height is 25 mm.

*Form*.—Shape of flower when viewed from the side: Upon opening, upper part: Flat. Upon opening, lower part: Flattened convex. Open flower, upper part: Flat. Open flower, lower part: Flattened convex.

Color:

*Upon opening, petals*.—Outermost petals: Outer Side: Red Group 46A. Inner Side: Red Group 46B. Innermost petals: Outer Side: Red Group 46A. Inner Side: Red Group 46B and 46C.

*Upon opening, basal petal spots*.—Basal petal spot, outermost petals: Outer Side: Yellow-Green Group 150D. Inner Side: Yellow-Green Group 146D. Basal petal spot, innermost petals: Outer Side: Yellow-Green Group 150D. Inner Side: Yellow-Green Group 146D.

*After opening, petals*.—Outermost petals: Outer Side: Red Group 46B. Inner Side: Red Group 53D. Innermost petals: Outer Side: Red Group 53D. Inner Side: Red Group 46D.

*After opening, basal petal spots*.—Basal petal spot, outermost petals: Outer Side: White Group 155D. Inner Side: White Group 155D. Basal petal spot, innermost petals: Outer Side: White Group 155D. Inner Side: White Group 155D.

General tonality: On open flower Red Group 45B. No change in the general tonality at the end of the 5$^{th}$ day. Afterwards, general tonality is Red Group 53C.

Petals:

*Petal count*.—Very double. Average Range: Approximately 70 petals under normal conditions.

*Petal reflex*.—Petals reflex slightly.

*Petal edge*.—Entire.

*Petal shape*.—Ovate. Apex shape is round. Shape of base is obtuse.

*Petal size*.—20-35 mm (l)×25-35 mm (w).

*Thickness*.—Average.

*Petal arrangement*.—Not formal. Quartered.

Petaloids: Limited numbers present.

*Petaloid count*.—Average of 3-8 per flower.

*Petaloid size*.—Petaloids are 8-10 mm (l) and 2-5 mm (w).

*Petaloid color*.—Color of inner side is Red Group 46D. Color of outer side is Red Group 53C.

*Petaloid texture*.—Thin.

*Margins*.—Undulated. Irregular.

*Petaloid shape*.—Most commonly deltoid, with some petaloids highly irregular. Apex: Deltoid. Base: Pointed.

Reproductive organs:

*Pistils*.—Average. Approximately 15 present. Stigmas: Location: Slightly superior in position to anthers. Color: Yellow-Green Group 144B. Styles: Length: Average 6-7 mm long. Color: Yellow-Green Group 144B.

*Stamens*.—Approximately 25 on average and regularly arranged. Anthers: Size: 0.5 mm long, on average. Pollen: Generally present. Color: Greyed-Orange Group 165B. Filaments: Color: Yellow Group 151D. Length: 5 mm, on average.

THE PLANT

*Growth*.—Moderate.

*Plant habit*.—Upright to bushy habit. When grown as a budded field plant, the average plant height is 80 cm and the average plant width is 40 cm.

*Stems*.—Stem color: Young wood: Yellow-Green Group 146B. Older wood: Yellow-Green Group 146B. Stem surface: Young wood: Smooth. Older wood: Smooth.

*Prickles*.—Present. Incidence: 7-8 per each 10 cm of stem. Size: Average length: 4 mm. Color: Immature prickles: Greyed-Orange Group 172B. Mature prickles: Greyed-Purple Group 185B. Senescing to Greyed-Orange Group 165A. Shape: Deeply concave. Anthocyanin: None observed.

*Leaves and leaflets*.—Normally 5 leaflets on normal leaves in middle of the stem. Venation pattern: Pyramidal net pattern. Leaf size: 160 mm (l)×130 mm (w). Abundance: Average. Texture: Rugose. Upper side of leaflet: Semi-glossy. Smooth. Under side of leaflet: Matte. Smooth. Color, mature foliage: Upper Leaf Surface: Green Group 137A. Lower Leaf Surface: Yellow-Green Group 146A. Color, juvenile foliage: Upper Leaf Surface: Green Group 137A. Lower Leaf Surface: Between Yellow-Green Group 146B and 146C. Anthocyanin intonation: None observed.

*Stipules*.—Size: 30 mm long. 4 mm between the distal tips of the stipules. Stipule color: Yellow-Green Group 146B. Anthocyanin: Midrib with intonations of Greyed-Purple Group 185D. Stipitate glands: Present in limited numbers. Margins: Very ciliated with stipitate glands. Shape: Apex: Apiculate. Base: Flat.

*Petiole*.—Length: Average of 8-10 mm. Diameter: Average of 2 mm. Petiole color: Yellow-Green Group 146B. Underneath: Smooth. Margins: With limited number of stipitate glands. Anthocyanin None observed. Prickles: Lacking.

*Petiole rachis*.—Length: 25-30 mm, on average. Diameter: 1 mm, on average. Color: Yellow-Green Group 146C. Margins: Limited number of stipitate glands. Prickles: Lacking.

*Leaflets*.—Size: Average size of the terminal leaflet is 70-80 mm (l)×40-45 mm (w). Shape: Base: Obtuse. Apex: Cuspidate. Margins: Serrated. Surface: Upper: Semi-glossy. Lower: Matte. Texture: Thick. Arrangement: Odd pinnate. Venation Reticulate.

Hips/seed formation: None observed.

Winter hardiness: To date, the variety has been grown successfully in Zones 5-9.

Disease resistance: Excellent resistance to powdery mildew (*Sphaerotheca pannosa*), rust (*Phragmidium disciflorum*), and blackspot (*Diplocarpon rosae*), diseases under normal growing conditions.

I claim:

1. A new and distinct variety of rose plant, as described and illustrated herein.

* * * * *

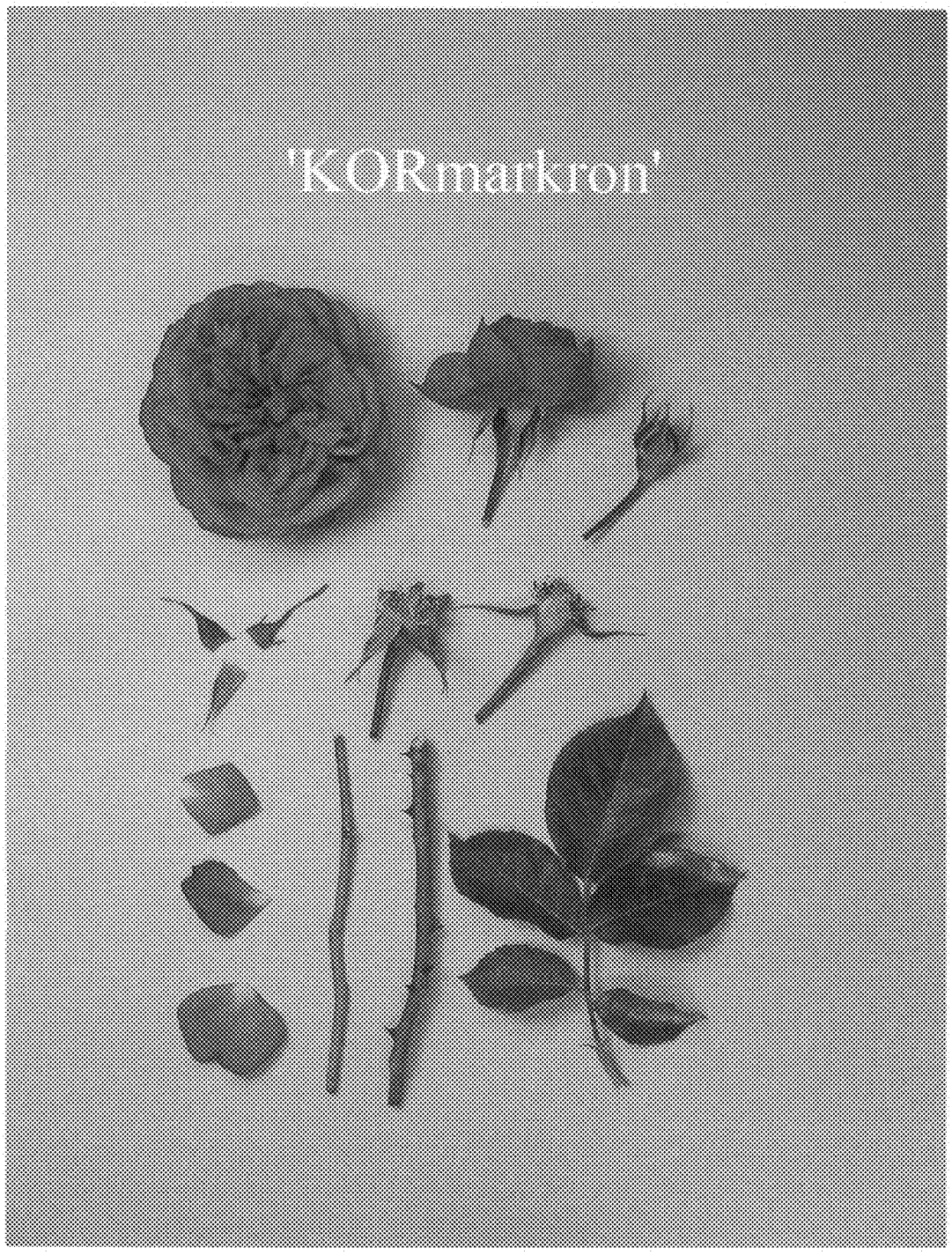
'KORmarkron'